US00RE42876E

(19) United States
(12) Reissued Patent
Heffel et al.

(10) Patent Number: US RE42,876 E
(45) Date of Reissued Patent: Nov. 1, 2011

(54) APPARATUS AND METHOD FOR OPERATING INTERNAL COMBUSTION ENGINES FROM VARIABLE MIXTURES OF GASEOUS FUELS

(75) Inventors: James W. Heffel, Lake Matthews, CA (US); Paul B. Scott, Northridge, CA (US); Chan Seung Park, Yorba Linda, CA (US)

(73) Assignee: The Regents of the University of California, Oakland, CA (US)

(21) Appl. No.: 12/769,408

(22) Filed: Apr. 28, 2010

Related U.S. Patent Documents

Reissue of:
(64) Patent No.: 6,612,269
Issued: Sep. 2, 2003
Appl. No.: 09/925,281
Filed: Aug. 8, 2001

U.S. Applications:
(60) Provisional application No. 60/225,017, filed on Aug. 11, 2000.

(51) Int. Cl.
*F02B 43/00* (2006.01)

(52) U.S. Cl. ..... 123/1 A; 123/494

(58) Field of Classification Search ..... 123/1 A, 123/3, 27 GE, 431, 494, 527, 575
See application file for complete search history.

(56) References Cited

U.S. PATENT DOCUMENTS 3,478,573 A 11/1969 King, Jr.
5,117,802 A 6/1992 Durbin
5,367,999 A * 11/1994 King et al. ..... 123/458
5,401,162 A * 3/1995 Bonne ..... 431/12
5,772,321 A 6/1998 Rhodes
5,787,864 A * 8/1998 Collier et al. ..... 123/436

FOREIGN PATENT DOCUMENTS

EP 0 348 245 6/1989
FR 1448236 6/1965
JP 62218647 9/1987

(Continued)

OTHER PUBLICATIONS

International Search Report from the International Searching Authority, International Application No. PCT/US01/25172, pp. 1 thru 7, (Dec. 27, 2001).

(Continued)

*Primary Examiner* — Noah Kamen
(74) *Attorney, Agent, or Firm* — John P. O'Banion

(57) ABSTRACT

An apparatus and method for utilizing any arbitrary mixture ratio of multiple fuel gases having differing combustion characteristics, such as natural gas and hydrogen gas, within an internal combustion engine. The gaseous fuel composition ratio is first sensed, such as by thermal conductivity, infrared signature, sound propagation speed, or equivalent mixture differentiation mechanisms and combinations thereof which are utilized as input(s) to a "multiple map" engine control module which modulates selected operating parameters of the engine, such as fuel injection and ignition timing, in response to the proportions of fuel gases available so that the engine operates correctly and at high efficiency irrespective of the gas mixture ratio being utilized. As a result, an engine configured according to the teachings of the present invention may be fueled from at least two different fuel sources without admixing constraints.

88 Claims, 8 Drawing Sheets

FOREIGN PATENT DOCUMENTS

JP 10220264 7/1997

OTHER PUBLICATIONS

Oehmichen, M.; "Liquid Hydrogen: Fuel of the Future," Wasserstoff als Motortriebsmittel, Deutsche Kraftfahrtforschung, vol. 68, pp. 1 thru 5, (1942). No translation available.

Norbeck, Joseph M.; Heffel James W. (Editor); "Hydrogen Fuel for Surface Transportation," Society of Automotive Engineers, p. 28, (1996).

Lynch, F., "Hydrogen Engines: Emissions and Performance," presented at SAE "Emissions from Alternative Fueled Engines," Toptec, San Antonio, Texas, Poster Presentation, pp. 1 thru 15, Dec. 9-11, (1991).

Lynch, F., "Near Term Introduction of Clean Hydrogen Vehicles via H2 CNG Blends," presented at Fourth Canadian Hydrogen Workshop, Toronto, Canada, pp. 1 thru 13, Nov. 1 & 2, (1989).

Hoekstra, R.L. et al., "Demostration of Hydrogen Mixed Gas Vehicles," Hydrogen Energy Progress X, Proceedings of the Tenth World Hydrogen Energy Conference, Cape Canaveral, Florida, pp. 1781 thru 1796, (1994).

Van Blarigan, P., "Development of a Hydrogen Fueled Internal Combustion Engineer Designed for Single Speed/Power Operation," SAE Paper 961,960, Future Transportation Technology Conference, pp. 1 thru 10, Sandia National Laboratories, Albuerqueque, N.M., Aug., (1996).

Hirsfelder, J.O. et al.; "Molecular Theory of Gases and Liquids," pp. 578-579, John Wiley & Sons, New York, N.Y., (1954).

"The Real Price of Gasoline," Inernational Center for Technology Assessment, Executive Summary, cover page + foreward + table of contents + pp. 1 & 2, Washington, D.C., (1998).

Thomas, C.E. et al.; Integrated Analysis of Hydrogen Passenger Vehicle Transportation Pathways, Directed Technologies, Inc., Draft Final Report, cover page + table of contents (3 pages) + pp. 1 thru 8, Nov. 27, (1996).

Thomas, C.E. et al.; Integrated Analysis of Hydrogen Passenger Vehicle Transportation Pathways, Directed Technologies, Inc., Draft Final Report, cover page + table of contents (5 pages) + pp. 1 thru 17, Revision 2, Mar., (1998).

* cited by examiner

APPARATUS AND METHOD FOR OPERATING INTERNAL COMBUSTION ENGINES FROM VARIABLE MIXTURES OF GASEOUS FUELS

Matter enclosed in heavy brackets [ ] appears in the original patent but forms no part of this reissue specification; matter printed in italics indicates the additions made by reissue.

CROSS-REFERENCE TO RELATED APPLICATIONS

This application claims priority from U.S. provisional application serial No. 60/225,017 filed on Aug. 11, 2000, incorporated herein by reference.

STATEMENT REGARDING FEDERALLY SPONSORED RESEARCH OR DEVELOPMENT

This invention was made with Government support under Contract No. DE-FC36-94G010039 awarded by the U.S. Department of Energy. The Government has certain rights in this invention.

REFERENCE TO A COMPUTER PROGRAM APPENDIX

Not Applicable

BACKGROUND OF THE INVENTION

1. Field of the Invention

The invention pertains generally to internal combustion engines utilizing gaseous fuels, and more particularly to a method and apparatus for operating an internal combustion engine at high efficiency from an arbitrary mixture of multiple gaseous fuels such as hydrogen and natural gas.

2. Description of the Background Art

The current use of fossil fuels, such as gasoline, diesel fuel, and natural gas, to power various forms of internal combustion engines, in particular those incorporated within motor vehicles, has a number of serious shortcomings in view of dwindling fossil fuel resources and the increasing awareness of the detrimental effects of pollution. The desire to enjoy abundant energy while striving for the benefits of clean air have led to the consideration of various alternative energy sources for powering equipment such as motor vehicles. The use of renewable forms of energy is highly preferred to assure that energy remains abundant despite dwindling fossil fuel resources.

In recent years, the desire to use clean, renewable, vehicle energy sources has been evidenced by a push toward the use of electrical vehicles. The adoption of electrical vehicles, however, has proceeded slowly and a number of electric vehicle manufacturers have discontinued sales. Despite the enormous expenditures to develop electric vehicles and recharging equipment, the fundamental shortcomings of the technology and infrastructure have never been overcome. It should be appreciated that, although electrical energy may be readily converted to mechanical energy without generating high emission levels, electrical energy storage within batteries has many inherent drawbacks, including the time required to recharge a battery, the cost of batteries, and the weight per unit of energy stored within a battery. In contrast, conventional internal combustion engines (ICE) powered from liquid or gaseous fuels may be readily "recharged" by refueling, while the fuels themselves provide about a thirty-fold increase in energy storage density when compared with battery energy sources. However, the drawbacks associated with emissions and other environmental concerns, as well as the non-renewable nature of these fossil fuels, remain.

In response to these concerns, a number of alternative fuels have been considered to reduce air-borne emissions while maintaining the convenience and energy storage efficiency that are inherent within a combustion process. Increasingly, attention is being focused on hydrogen as a fuel for use within both internal combustion engines (ICE) and fuel cells. When utilized within an ICE, it should be appreciated that hydrogen provides a clean burning renewable energy source that may be readily produced. Home hydrogen refueling appliances have been proposed for use with hydrogen vehicles which are small in size and capable of generating sufficient hydrogen to power a vehicle for a trip spanning a few hundred miles. Vehicles incorporating hydrogen powered internal combustion engines have been studied and have been found to provide significant benefits from lowered emission levels and fuel renewability.

On-board vehicle energy reforming is also being considered, wherein a hydrogen powered vehicle is provided with a fuel reformer that converts the available fossil fuel to hydrogen gas which is utilized to operate a hydrogen combustion engine or a hydrogen fuel cell. A number of disadvantages exist, however, with regard to the adoption of on-board reforming for the purposes of facilitating the introduction of vehicles which operate from hydrogen fuel cells.

The adoption of hydrogen as an energy source has been a slow process, perhaps due in part to the inherent difficulty of changing an existing infrastructure to accommodate the use of hydrogen. The present infrastructure is lacking in both vehicles and fueling facilities that are capable of using, or distributing, hydrogen. Changing the present infrastructure to provide hydrogen distribution while synchronously developing and deploying hydrogen-fueled vehicles is a formidable challenge. It will be appreciated that vehicle manufacturers are resistant to invest in the development and marketing of hydrogen vehicles until the fuels are readily available, while fuel manufacturers are resistant to invest in widespread hydrogen production and distribution facilities until vehicles exist for consuming hydrogen fuels.

On the other hand, natural gas is a widely distributed form of gaseous hydrocarbon fossil fuel that typically comprises methane, although proportions of ethane, propane, and butane may also he present. Presently, an infrastructure exists to distribute natural gas for use in many applications, including motor vehicles. It should be appreciated that, at one point in recent history, automobiles and fuel distribution facilities were being rapidly adapted for the use and distribution, respectively, of natural gas because the prices of natural gas were well below that of gasoline and the conversion process was inexpensive. The transition from natural gas to hydrogen gas may appear trivial in that vehicles configured for burning natural gas may be reconfigured to exclusively burn hydrogen gas. One key difference between these fuels, however, is the energy density contained per cubic foot. Natural gas provides a significantly higher energy density than hydrogen gas, and consequently, an engine configured to operate on hydrogen gas, instead of natural gas, requires a higher fuel volume per combustion cycle to deliver a given rated horsepower and torque. Therefore, it will be appreciated that combustion variables must be reconfigured to provide for the burning of hydrogen gas. Consequently, the adoption of hydrogen gas as a "replacement" for natural gas would not solve the inherent infrastructure problems associated with the introduction of a new incompatible fuel source, and the conversion of vehicles to hydrogen could only be expected after an adequate hydrogen fuel distribution network had been established.

The use of hydrogen as an energy source within internal combustion vehicles has additional aspects that should be appreciated. First, although the hydrogen combustion process involves burning increased volumes of gaseous fuel, the resulting emissions contain lower levels of air pollutants and carbon dioxide than a comparable engine generating a give horsepower when operating from a natural gas fuel source. Second, hydrogen is a renewable fuel source that may be generated from a number of low-cost processes, whereas natural gas is a limited fossil fuel resource. It is anticipated, therefore, that the cost of fossil fuels will increase as the supply dwindles and that the low cost of generating renewable hydrogen will become increasingly attractive. The widespread use of hydrogen in future vehicles should then result in a lower cost per mile than that obtainable through the use of non-renewable fossil fuel resources.

Despite the inherent emission and renewability advantages of hydrogen use, the implementation of hydrogen vehicles has proceeded slowly. It will be appreciated that convenient operation of a hydrogen vehicle over distances requiring refueling has not been possible thus far due to a lack of hydrogen fuel distribution facilities. Experimental hydrogen vehicles are therefore only capable of operating within a limited commute radius about a facility-based refueling station.

The deployment of a substantial number of vehicles capable of operating from hydrogen would be an impetus for establishing the necessary elements of a hydrogen-fueling infrastructure. An internal combustion engines fueled by pure hydrogen would be capable of operating over a large range of fuel-air mixture ranges, including operation at a fuel-air mixture that is as lean as one fourth of stoichiometric fuel. It will be appreciated that in order for the hydrogen to he completely consumed a specific volume of air is required. The combustion process is generally given by the following formula:

$$2H_2+(O_2+3.77N_2)=>2H_2O+3.77N_2 \quad (1)$$

As a result of the combustion process, a total of 4.77 volumes of air are required for every 2 volumes of hydrogen utilized in the combustion process. This ratio is commonly referred to as a stoichiometric mass ratio of 34.3:1.

Optimal efficiency with a hydrogen ICE is attained at equivalence ratio $\phi$ of about 0.4, whereas a natural gas engine typically operates slightly lean of stoichiometric. By way of reference, it will be appreciated that the equivalence ratio is defined as the fuel/air mixture ratio normalized by the stoichiometric fuel/air mass. Efficiency is extremely important for hydrogen fueled vehicles, as the available fuel storage volume limits vehicle range. The hybrid electric configuration is therefore attractive for hydrogen fueled vehicles due to the ability to set up the engine to operate at substantially constant speed at peak efficiency consistent with low emissive output. Furthermore, the flame speed of a hydrogen-air mixture is substantially above that of a mixture of natural gas and air, although the speeds are decreased as the mixtures are made more lean. Fixed mixtures of hydrogen and natural gas have been developed, most notably Hythane™ which is a mixture of natural gas containing about 15% hydrogen, wherein the hydrogen contributes approximately 5% energy of the combustion energy. The Florida Solar Energy Center has experimented with mixtures having fixed percentages of hydrogen and methane. These mixtures utilize specific ratios of hydrogen up to about 36%, by volume, within the natural gas to contribute up to approximately 12% of the gaseous fuel energy. Researchers noted that the addition of hydrogen to natural gas aids lean operation and clean burning, and that either pure hydrogen or 30% hydrogen/natural gas can fuel an ICE so as to meet the EZEV (Equivalent Zero Emissions Vehicle) standard.

This body of work on the use of hydrogen fuel, and fuels containing hydrogen, indicates that efficient combustion may occur with natural gas, hydrogen, or a specific mixture thereof. However, because the fuel metering and timing of a vehicle is determined by the fuel being utilized, these fuels require that the engine be designed or specifically configured for use with a chosen fuel mixture. This imposes significant limits on the fuel mixtures that can be employed.

Therefore, a need exists for equipment and methods to ease the transition from conventional fossil based fuels to the widespread adoption of hydrogen fuel. The present invention satisfies that need, as well as others, and overcomes the deficiencies of previously developed vehicle energy solutions.

BRIEF SUMMARY OF THE INVENTION

The present invention generally comprises a method and apparatus for operating an internal combustion engine from any arbitrary mixture of gaseous fuels. More particularly, the present invention comprises a variable gaseous fuels (VGF) engine which is capable of operating from a fuel source containing an arbitrary mixture of natural gas and hydrogen gas. Note that in the present invention the mixture can vary as opposed to being fixed. Accordingly, the terms "variable gaseous fuels" and "VGF" as used herein should not be confused with the use of conventional mixed fuels having a fixed mixture ratio or "composition", such as "Flex Fuel" which comprises a fixed ratio of gasoline and methanol, or "Hythane™" which comprises a fixed ratio of hydrogen and natural gas.

By way of example, and not of limitation, the VGF engine of the present invention determines the ratio of the available gases mixed within, or being received from, the vehicle's fuel storage tank and modulates the parameters of the combustion process accordingly to provide efficient combustion for any arbitrary mixture of gases. It will be appreciated that the admixed gaseous fuels for operating the VGF engine may be received from a single pressurized fuel tank, or from any alternative mechanism capable of supplying a mixture of hydrogen and natural gas.

A VGF engine according to the invention is preferably configured for burning any arbitrary mixture of natural gas and hydrogen. In operation, the VGF engine measures the relative mixtures of the two gases in the fuel supply, such as within the fuel storage tank or in the fuel connections that lead from the fuel tank to the engine, and adjusts combustion parameters accordingly. The amount of fuel being metered into the engine is then modulated in response to the measured ratio of gases within the mixture and the associated energy densities thereof.

The invention includes means for determining the gaseous fuel composition so that combustion parameters may be adjusted, such as fuel volume and ignition timing, to assure efficient operation for any given mixture of gaseous fuel. In gaseous mixtures of hydrogen and natural gas, for example, the fuel flow rate must be increased as the ratio of hydrogen gas to natural gas is increased due to the lower energy density of the hydrogen gas. Accordingly, a VGF engine according to the present invention preferably includes fuel composition sensors that are capable of measuring the gaseous fuel composition, as well as an electronic engine control module (ECM) that scales the amount of fuel being metered into the combustion chamber and that optionally modifies additional combustion parameters such as ignition timing, valve timing, and so forth. By measuring the gaseous mixture ratio within the fuel storage tank or in the fuel connections that lead from the fuel tank to the engine, the control electronics can compensate for the fuel mixture before any improperly adjusted combustion cycles can occur.

It will be appreciated that the gaseous fuel composition sensor may he implemented in a number of ways that allow the mixture ratio of the composite gases to be determined. Although the term fuel composition sensor is utilized herein, the sensor could alternatively be referred to as a fuel mixture ratio sensor, and so forth, without departing from the present invention.

A number of forms of internal combustion engines, such as conventional piston engines, rotary engines, sterling engines, and so forth, are capable of being separately configured to operate from fuels having different combustion properties and may he adapted for operation from a variable gaseous mixture of fuels according to the teachings of the present invention. It will be appreciated that sensing gaseous fuel composition and adjusting combustion variables accordingly are functions that may be readily incorporated within modern internal combustion engines, since modern engines are being increasingly designed toward full electronic control of all aspects of the combustion process, such as fuel metering, ignition timing, valve operation, and so forth.

The gaseous fuel composition (mixture ratio) may be determined in a number of ways by analyzing one or more differentiable characteristics of the gaseous fuel supply prior to combustion, or by analyzing combustion results, or by combinations thereof. For example, characteristics which may be utilized to differentiate hydrogen gas from natural gas include thermal conductivity, infrared signature, sound velocity, and so forth. One or more of these characteristics may be detected using sensors and the resultant data used to determine the mixture ratio. It should be appreciated that the characteristics of the gas which are measured for determining a gaseous mixture ratio would preferably be substantially immune to changes in temperature, pressure, water vapor, selected additives, and similar non-mixture related characteristics, or would allow non-mixture related variables to be eliminated by electronic or computational means.

For example, measuring the thermal conductivity of a gaseous fuel mixture can be performed with a thermal conductivity sensor which communicates a thermal conductivity signal to a programmed electronic engine control module. The thermal conductivity signal is interpreted by the ECM to determine a fuel quantity compensation value based substantially on relative energy densities within the constituent components of the gaseous mixture. The ECM then modulates the quantity of gaseous fuel being metered into the combustion chamber in response to its anticipated energy density as based on the fuel composition information received from the fuel composition sensor. It will also be appreciated that a number of internal combustion engines utilize a fuel metering means, such as fuel injectors which meter fuel to the cylinders in response to the pulse-width of a received gas metering signal.

The ECM therefore meters an appropriate volume of gaseous fuel into each cylinder in response to the composition of the available gaseous fuel, along with traditional fuel metering determinants such as throttle setting, RPM, temperature, and the like. Incorporating gaseous fuel composition sensing and the ability to adjust fuel metering and other optional combustion parameters in response to fuel composition results in a VGF engine according to the present invention which is capable of being efficiently operated from a source of gaseous fuel which contains any proportion of natural gas and hydrogen.

An object of the invention is to expedite the transition from the use of fossil fuels to a renewable hydrogen energy source by providing an engine capable of operating on any mixture of either fuel source.

Another object of the invention is to provide a variable gaseous fuel engine capable of being utilized within a motor vehicle.

Another object of the invention is to provide an engine capable of properly combusting an arbitrary mixture of two gases contained within a single fuel tank.

Another object of the invention is to provide a method for determining the composition of a gaseous mixture of natural gas and hydrogen gas.

Another object of the invention is to provide an electronic engine control module that is capable of responding to the composition of the gas source by modulating combustion parameters such as fuel metering and ignition timing.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DETAILED DESCRIPTION OF THE INVENTION

For illustrative purposes, the present invention is embodied in the apparatus and method generally shown and described herein with reference to FIG. 1 through FIG. 10. It will be appreciated that the apparatus may vary as to configuration and as to details of the parts, and that the method may vary as to the specific steps and sequence, without departing from the basic concepts as disclosed herein.

In general terms, the present invention comprises a variable gaseous fuel (VGF) engine that is capable of operating on any mixture ratio of a first gaseous fuel, such as hydrogen, and a second gaseous fuel, such as natural gas. It will be appreciated that the invention provides for the operation of a vehicle, or other gaseous fuel internal combustion engine device, from any arbitrary mixture of hydrogen and natural gas, and therefore creates a bridge to facilitate the transition from dwindling fossil fuels to a renewable hydrogen energy source.

Vehicles incorporating VGF engines according to the present invention are capable of utilizing currently available natural gas and transitioning to hydrogen fuel as sources of supply become more readily available. A VGF engine equipped vehicle according to the present invention is capable of operating from any available gaseous source of either gas or combined mixture of the two gases. The VGF engine is configured for sensing the composition (mixture ratio) of the available gaseous fuel utilizing an electronic sensor capable of differentiating one or more characteristics of a first gaseous fuel from a second gaseous fuel and adjusting combustion parameters accordingly. Important combustion parameters to be controlled include fuel quantity and ignition timing so that efficient combustion may be achieved regardless of the specific gas mixture ratio being combusted.

Figure 1:
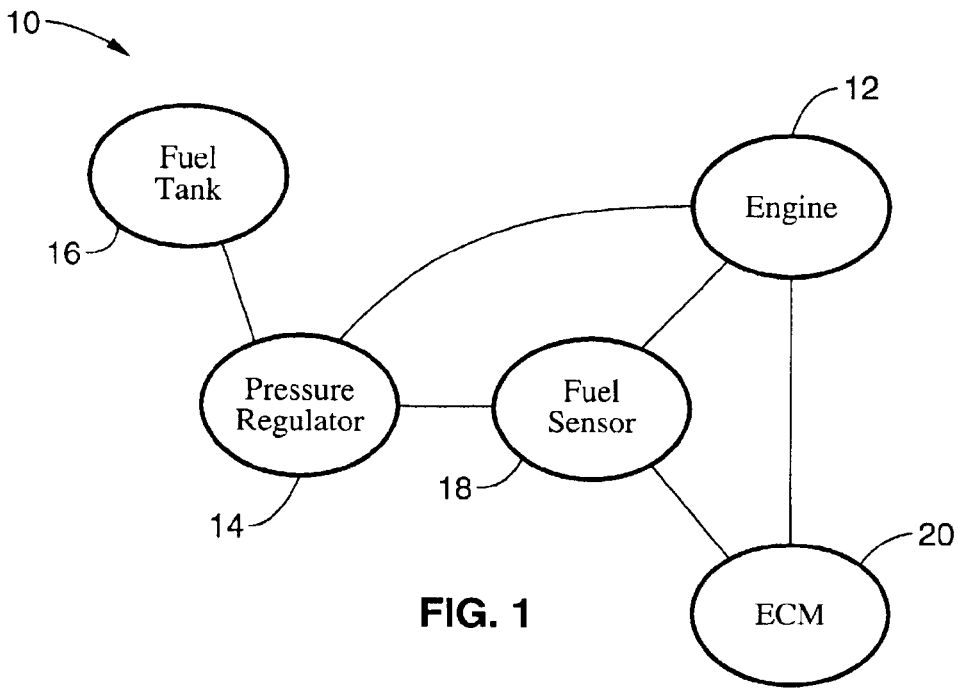
FIG. 1 is a functional block diagram of a variable gaseous fuels engine according to the present invention.

FIG. 1 illustrates the elements of a VGF engine 10 according to the present invention which generally comprises an internal combustion engine 12 receiving a mixture of gaseous fuels through a pressure regulator 14 from a gaseous fuel tank 16. Combustion within engine 12 is controlled by sensing the gaseous fuel mixture within fuel composition sensor 18, the information being utilized by an engine control module 20 that controls parameters of the combustion process within internal combustion engine 12. Designing or configuring an engine for VGF operation according to the present invention requires the addition of a fuel composition sensing means and an engine control system capable of modulating the gaseous combustion volumes in response to the composition of the gas being received. It should be appreciated, however, that the additional sensors and control processing to provide VGF operation are easily incorporated within modern engines that are typically designed using electronic control systems which control an increasing number of combustion parameters.

Variable gas mixtures may be stored within any gaseous fuel tank 16 system capable of storing natural gas. Typically, a pressure regulator 14 is utilized on the fuel tank 16 to reduce tank pressure to a constant value, typically about 10bar (145 psi), prior to receipt by the gaseous mixture metering system within engine 12. However, it should be appreciated that the need for a pressure regulator, and the pressure to which such a regulator is adjusted, depends on the fuel metering devices incorporated within the engine. The metering system of engine 12 is responsive to the measured mixture ratio of hydrogen gas to natural gas, while additional combustion parameters, such as ignition timing, may also be adjusted.

Figure 2:
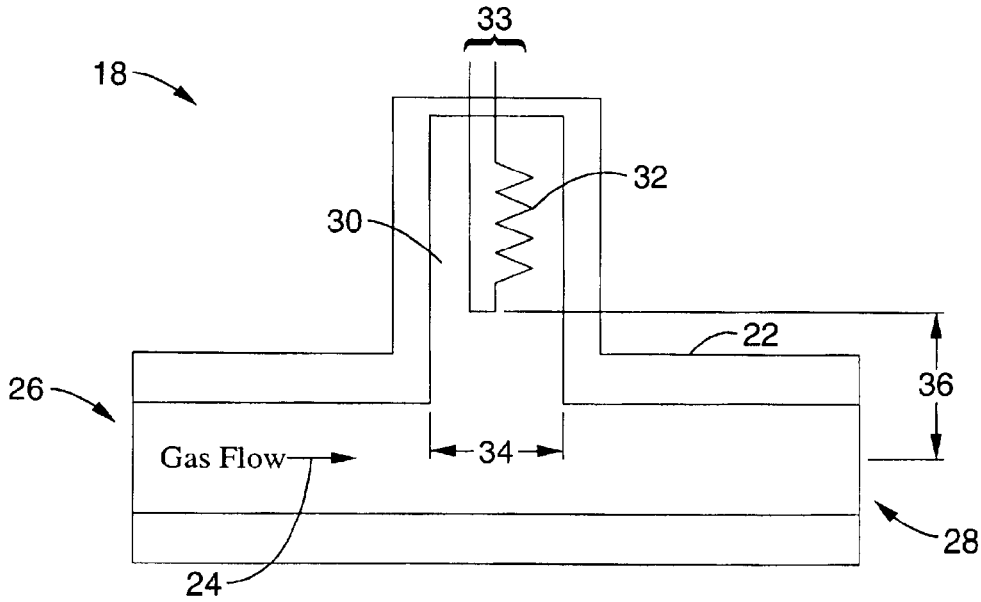
FIG. 2 is a cross-sectional schematic view of a gas composition sensor according to an aspect of the present invention, shown with a heated filament being retained within the gas mixture from which the gas composition may be detected.

FIG. 2 illustrates a fuel composition sensor 18 capable of determining the gaseous mixture ratio (composition) of the available gaseous fuel. Fuel composition sensor 18 is preferably positioned toward an engine fuel intake to determine combustion parameters based on the composition of incoming variable gaseous fuels.

An example of a sensor suitable for fuel composition sensor 18 is a thermal conductivity sensor which is retained in fluidic contact, or substantially surrounded by, the available gaseous fuels. One form of electronic sensor that may be utilized has been developed by the College of Engineering "Center for Environmental Research and Technology" (CE-CERT) at the University of California, Riverside.

It will be appreciated that hydrogen and natural gas exhibit markedly dissimilar thermal conductivity values, which allows gas composition of a mixture of hydrogen and natural gas to be readily determined from the measured thermal conductivity. The composition of a natural gas/hydrogen blend may be readily determined from the output of the thermal conductivity sensor under a set of given conditions. When positioned within the gaseous intake of the engine, the thermal conductivity sensor outputs a signal that is indicative of the mixture ratio of the received gaseous fuel at the given temperature and pressure conditions. The thermal conductivity sensor may therefore be utilized as an input to a "multiple map" engine control module which controls the parameters of combustion within the internal combustion engine, such as fuel injectors and ignition timing. It will be appreciated that additional engine parameters may also be controlled to optimize engine operation for the given fuel mixture, such as valve actuation, engine cooling, and so forth.

Fuel composition sensor 18 should be positioned to establish fluidic contact with the gaseous fuel that will be received by the combustion engine. The sensor preferably comprises a housing 22 configured with one or more passageways, such as a passageway 24 having an intake end 26 and an output end 28. Preferably fuel mixture sensor 18 is located along the pathway by which the gaseous fuel is conveyed to the combustion chamber of the engine.

By way of example, a section of fuel flow passageway 24 receives a mixture of gaseous fuel from a gaseous fuel storage tank 16 within intake end 26 which is output through output end 28 to pass the gaseous fuel mixture to internal combustion engine 12, wherein it will be routed past a fuel metering device to one or more combustion chambers. Sensing of the fuel composition is illustrated in a preferred configuration within a separate chamber 30 which partially isolates the fuel flow sensor from changes in convective cooling that occur in response to variations of gas flow rate. A thermal conductivity sensor element, comprising filament 32 with electrical connections 33, is positioned within chamber 30.

A quantity of energy is input to the filament so as to heat the filament to a temperature above that of the gaseous fuel mixture which is in fluidic contact with the filament. The temperature attained by the filament within the gaseous fuel mixture is moderated by conductive energy losses which depend on the thermal conductivity of the surrounding gaseous fuel. For example, given any predetermined level of filament heating current, the temperature of the filament when retained in fluidic contact with hydrogen will be at a lower temperature than the same filament under identical conditions retained in fluidic contact with natural gas, due to the higher thermal conductivity of hydrogen gas which conducts increased levels of thermal energy away from the filament. The increased thermal conductivity of the hydrogen gas increases the amount by which the temperature of the filament is moderated by the conductive cooling. Given a sufficient difference between the thermal conductivity properties of two gases, such as exist between hydrogen gas and natural gas, the composition of the gaseous fuel may be determined. Energy is supplied to filament 32 by electrical connections 33 through which current is induced to flow through filament 32, while the voltage expressed across the filament as a result of the current flow is substantially indicative of the temperature of the filament in response to the thermal conduction of the surrounding gas. Stated another way, energy is dissipated from passing a first electrical current of sufficient amperage to heat the filament to a temperature which exceeds the gaseous fuel temperature. The thermal conductivity of the gaseous fuel is then determined by analyzing the conductive heat dissipation which occurs, as exhibited by the moderation of filament temperature, in response to the thermal conductivity of the gaseous fuel at the elevated filament temperature. It will be appreciated that increasing the amount of energy dissipated within the filament, and thus the amount by which the filament temperature exceeds the gaseous fuel temperature, generally increases the resultant signal which is generated by the thermal conductivity sensor due to the increased amount of conductive heat dissipation.

A number of methods exist for determining the temperature of the gaseous fuel proximal to gaseous fuel composition sensor 18, such as by utilizing a temperature sensor or another thermal conductivity sensor. One preferred method of sensing gaseous fuel temperature utilizes the same thermal conductivity type gaseous fuel composition sensor 18 operating in a different sensing mode. It should be appreciated that the resistance of the sensing element, filament 32, within gaseous fuel composition sensor 18 changes in response to the amount of electrical current flow and the temperature of filament 32. As a result, the passage of very small currents through the filament, insufficient to substantially alter filament temperature, provides a means for determining gaseous fuel temperature. It is only upon substantially increasing filament current to cause sufficient filament heating that the thermal conductivity of the surrounding gaseous mixture may be determined from the convective losses and the gas fuel composition calculated from the thermal conductivity.

While gaseous fuel composition sensor 18 has been described as being preferably located within the gaseous fuel intake of the engine, it should be appreciated that the fuel composition sensor may be alternatively positioned within the gaseous fuel storage tank, or within a device that is in gaseous contact thereof. It should be appreciated that positioning the sensor in the fuel intake can provide increased accuracy because the fuel mixture ratio that exists within the gaseous fuel lines near the fuel intake of the engine may not change simultaneously with a change in the mixture ratio of the tank, such as immediately following refueling of the gaseous fuel tank. Therefore, sensing the fuel mixture ratio at the intake can provide improved composition accuracy as the mixture ratio is sensed just prior to combustion. It should also be appreciated, however, that an auxiliary, or alternative, fuel mixture ratio measurement system can be performed as a post-combustion fuel ratio measurement. Information received from a post-combustion system would be preferably utilized for performing minor adjustments to the gas flow and engine operation, otherwise complications can arise in response to rapid gas mixture ratio changes.

Filament 32 preferably comprises a metallic resistance wire. By way of example, a Tungsten filament may be utilized, that preferable incorporates approximately two to ten percent Rhenium. One preferred filament material is manufactured by GOW-MAC Instrument Company which comprises Tungsten having approximately five percent Rhenium. A number of factors should be considered when selecting the material, gauge, and structure of the filament, including the temperature, corrosiveness and/or oxidation characteristics of the material to be analyzed. It will be appreciated that within a flowing environment of hydrogen gas and natural gas (which typically comprises about 80% methane), the oxidative impurity level within the fuel gas and the excitation current level utilized are important determining factors of sensor longevity. Filament 32 is preferably located within a chamber 30 that is retained in fluid communication with the passageway through which the gaseous fuel mixture flows. Chamber 30 is shown configured as a "T-shaped" branched line to desensitize the fuel mixture sensor 18 to the effects of convective flow.

EXAMPLE 1

Care should be taken in designing the structure of the fuel sensor as the internal diameter 34 of the branched line for the sensing element and the distance between sensor element and fuel flow line 36 have been found to be important considerations in providing an adequate sensor signal level with a sufficiently rapid response time. By way of example, a suitable fuel sensor structure was fabricated with a chamber having a diameter 34 of about one-half centimeter (0.53 cm actual diameter used in testing) whereas filament 30 was offset 36 from the center of the gas flow passageway by a distance of about two centimeters (2.3 cm actual offset utilized in testing). It will be appreciated therefore that high signal levels and low susceptibility to gaseous flow rate were obtained with the offset distance being approximately four times (4×) that of the chamber diameter. It should also be appreciated, however, that the filament may be isolated from the convective flow using alternative methods known to one of ordinary skill in the art without departing from the teachings of the present invention. A constant current source was utilized for heating the wire, and a digital voltmeter with differential input was used to measure the voltage of the filament exposed to the gaseous fuel flow.

It will also be appreciated that inclusion of non-filament voltage drops, such as those which occur within the wiring connecting the current source to the filament, will reduce the accuracy of filament voltage measurement and thereby the accuracy of the computed fuel composition. At low current levels the resistance of the filament is indicative of filament temperature which should be largely determined by the temperature of the gaseous fuel surrounding the filament. The resistance of the filament may be determined by dividing the measured filament voltage by the applied filament current according to the application of Ohm's Law, $R=V/I$. Upon applying a sufficient level of current to the filament, it begins heating up toward an equilibrium temperature that is in excess of the surrounding gaseous flow. The amount of resultant temperature increase for a given heating current level is subject to the thermal conduction of the filament within the surrounding gaseous fuel composition. The large difference in thermal conductivity between hydrogen gas and natural gas allow the thermal conductivity value for the gaseous fuel mixture to be used to differentiate the relative composition of the gaseous mixture. Determinations of gaseous fuel composition are preferably performed as calculations, or table lookups, based on empirically derived equations or mappings for the given filament structure under the given operating conditions.

EXAMPLE 2

Figure 3:
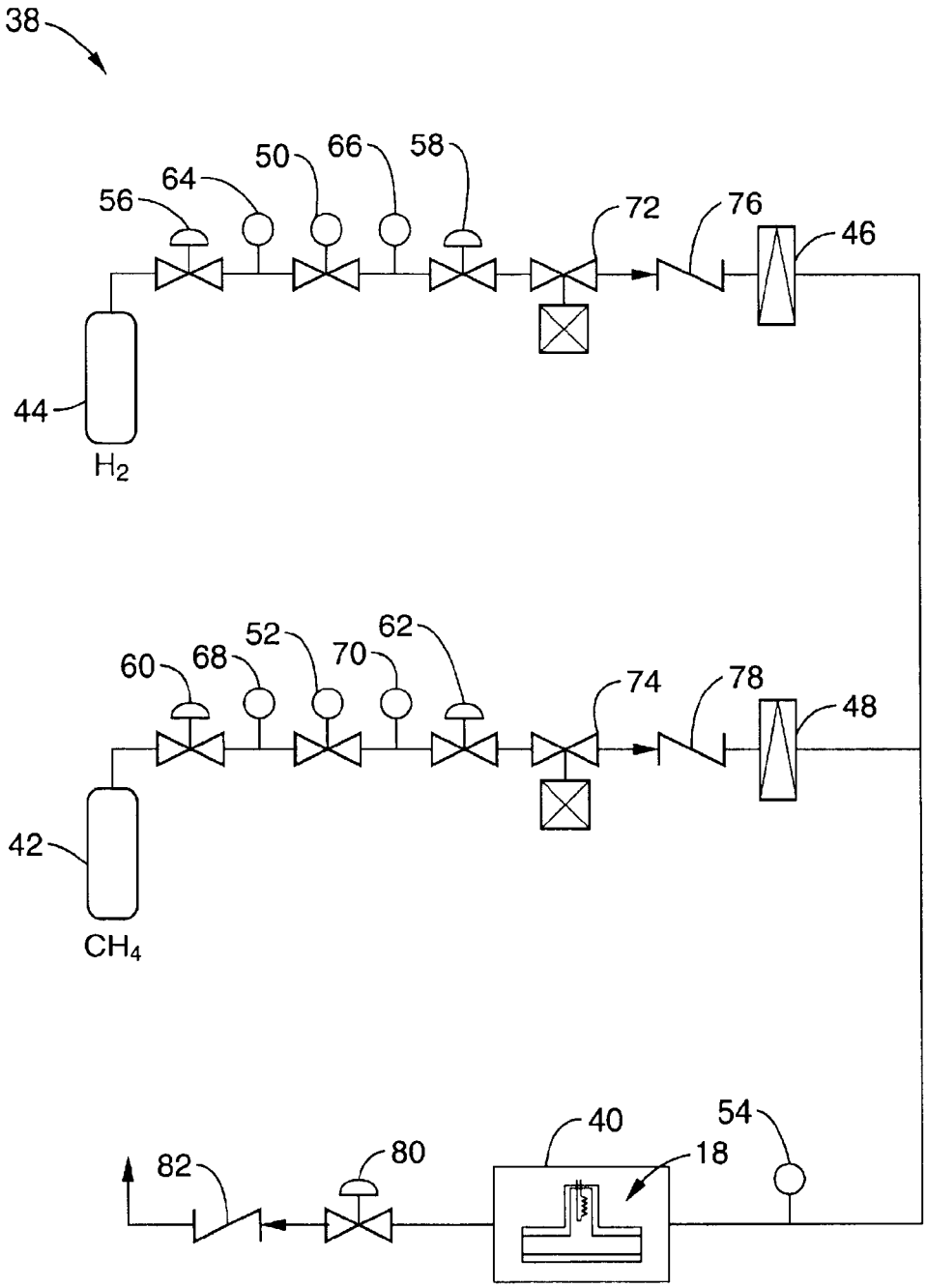
FIG. 3 is a schematic diagram of a sensor test bench utilized within the present invention for testing aspects of gaseous mixture sensing.

FIG. 3 illustrates a sensor test bench that was utilized for testing gaseous fuel composition sensor 18 as shown in FIG.

2. Test measurements were taken with fuel composition sensor 18 positioned within a temperature controlled oven 40. Oven temperature was measured utilizing an integrated circuit temperature sensor, specifically a model LM35 from National Semiconductor Incorporated®. The temperature sensor was utilized to control the temperature in conjunction with a personal computer to provide feedback for any desired value from ambient temperature to about 350 degrees Kelvin. Two kinds of calibration were performed with sources of pure methane 42 or pure hydrogen 44 that could be fed into fuel composition sensor 18 simultaneously, or sequentially, with the operation of a solenoid valve. The desired gas flow rate was adjusted by a needle valve and a ball flow meter 46, 48 for a range of flow situations from a static, no flow condition, to about two liters per minute. A calibration measurement of the resulting actual flow rate was observed from the motion of a soap bubble meniscus in a burette and gas pressure was adjusted with pressure regulators 50, 52, and the pressure value was sensed by pressure transducer 54, such as a Bourns Incorporated® model ST3100 pressure transducer capable of registering pressure from zero to two hundred pounds per square inch absolute (0-200 psia). Additional manual valves 56, 58, 60, 62, are shown for regulating the pressure along the gas line, said pressure capable of being registered on pressure gauges 64, 66, 68, 70. The connection of the gas sources can be controlled with solenoid valves 72, 74 and a pair of check valves 76, 78. The output from the gaseous fuel composition sensor 18 was controlled with manual valve 80 and the gaseous fuel passed through another check valve 82.

Figure 4:
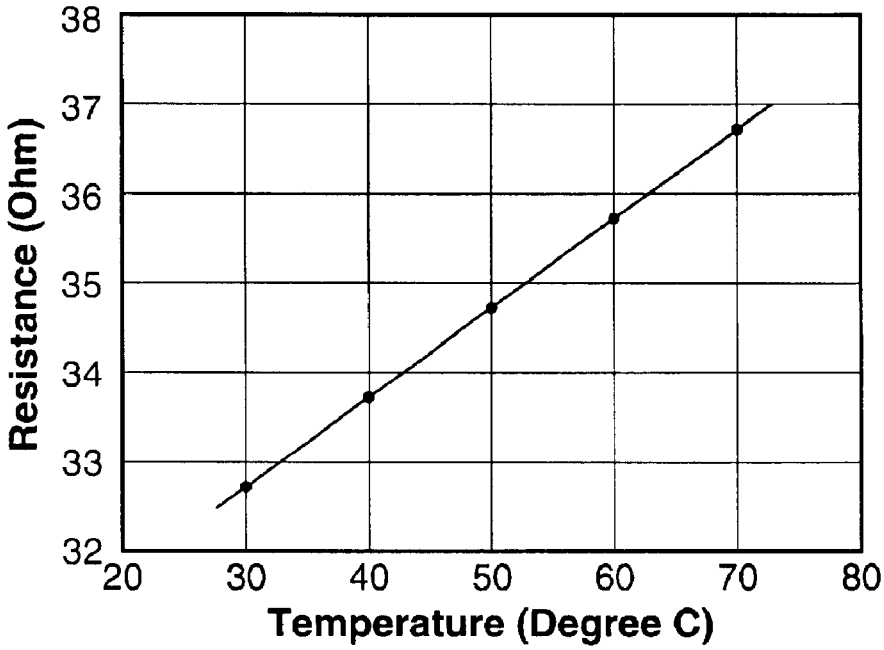
FIG. 4 is a graph showing filament resistance within a gaseous mixture sensor according to an embodiment of the present invention in response to temperature changes.

FIG. 4 illustrates typical results from testing of gaseous fuel composition sensor 18 with a plot of resistance change as a function of gas temperature with a value of filament current set at one milliampere (1 mA). The level of filament current was set to a minimum value consistent with the accuracy limitations of the equipment (0.1 mv voltmeter resolution) to minimize self heating effects. The amount of self-heating created from filament currents of up to a few milliamperes result in energy dissipation on the order of fractions of a microwatt and thereby generate a negligible temperature change. The current utilized for determining the temperature of gaseous flow should therefore be kept below a maximum of about ten milliamperes (10 mA), and preferably at or below a few milliamperes (2 mA–4 mA). A positive resistance change will be exhibited for a positive change in temperature when utilizing metallic materials for the filament of the thermal conductivity sensor. The relationship between temperature and resistance can be expressed as a simplified Callendar-Van Dusen equation:

$$R_T=R_0(1+\alpha T) \tag{2}$$

wherein $R_T$ is the resistance in ohms at temperature T, $R_0$ is the resistance in ohms at T=0° C. and $\alpha$ is the temperature coefficient at T=0° C. in ohms/ohms/° C. $R_0$ and $\alpha$ are calculated as 30.19±0.11 Ω and $(32.4\pm0.23)\times10^{-4}$ Ω/Ω/° C. with a 95% confidence level, respectively, from the slope and intercept exhibited within FIG. 4. Utilizing Eq. 2 and the associated constants, the gas temperature was measured with an accuracy of ±1° C. without utilizing additional temperature sensors or compensating for the small amount of current injected into the filament of the sensor.

Figure 5:
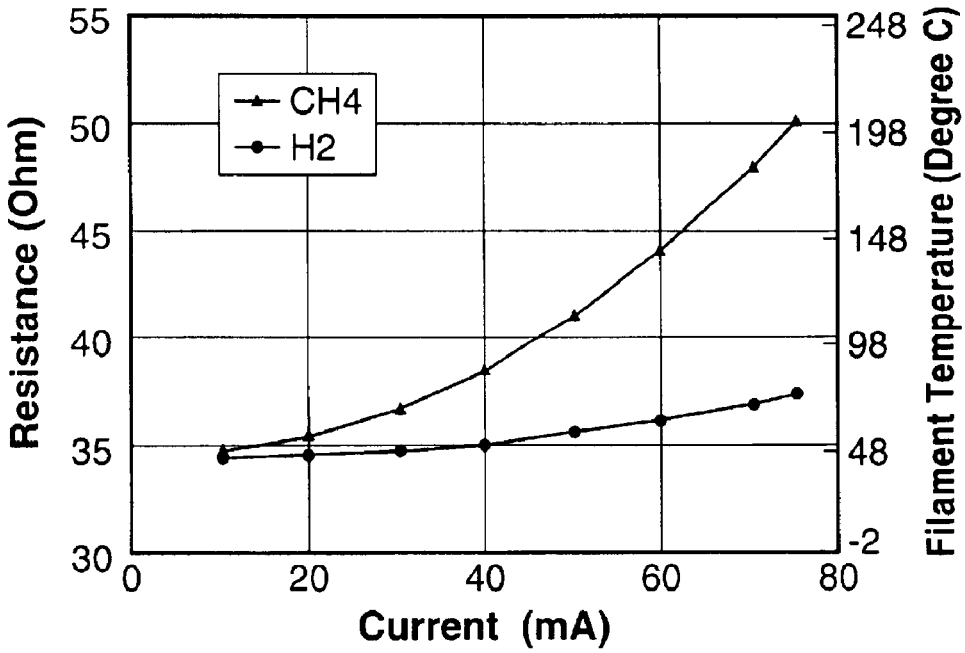
FIG. 5 is a graph showing filament resistance at different filament currents when exposed to either hydrogen gas ($H_2$), or natural gas which typically comprises a major percentage of methane gas $CH_4$.

FIG. 5 illustrates changes in filament resistance at various injected currents levels for each of the gases, specifically hydrogen $H_2$ and methane $CH_4$. The plot of filament resistance for hydrogen gas illustrates that filament heating is less when the filament is surrounded by hydrogen gas that it is when the filament is surrounded by natural gas. The difference in filament heating characteristics is due to the higher thermal conductivity of hydrogen such that more heat energy is dissipated from the filament into the surrounding hydrogen. The thermal conductivity measurements were performed at atmospheric pressure with a wall temperature of forty seven degrees Celsius (47° C.). In the low current region below ten milliamperes (10 mA), as discussed above, the sensor precision was not adequate to measure the gas composition, because the resistance value was largely indicative of gas temperature. Increasing the filament current above ten milliamperes (10 mA) dramatically increased the signal levels, thereby allowing thermal conductivity to be accurately registered. It should, however, be appreciated that filament longevity is inversely related to increased levels of filament current. In the present embodiment, filament current was set for about eighty milliamperes (80 mA), which is well below the two hundred milliampere (200 mA) maximum current suggested by the filament manufacturer, and which provides adequate sensitivity for mixture ratio detection. The present embodiment was found to tolerate substantial changes in the gaseous flow rate, up to and in excess of one liter per minute, without noticeable convective filament cooling. A high tolerance to flow rate variation is preferable within the application so that mixture ratios may be calculated without compensating for gaseous flow rate. A linear increase in sensor signal was observed within the tests as the body temperature of the sensor increased, therefore, sensor body temperature should be measured and used for compensating the fuel composition measurement. Alternatively, the filament mounting block may be held at a constant temperature with a sufficiently low gas flow rate so that the gaseous fuel mixture equilibrates at the mounting block temperature.

The effect of gas pressure was shown to be more complex than other gaseous mixture ratio variables. Theoretically the filament temperature, and thus the resistance of the sensor, is reduced by the amount of gaseous thermal conduction which occurs. The amount of gaseous conduction that occurs is determined by the thermal conductivity of the gas, κ, which defines the proportionality between heat flux and temperature gradient. Thermal conductivity is generally represented by the kinetic theory of gases.

$$\kappa=K\sqrt{(T/m)/S} \tag{3}$$

In Eq. (3) the value T1 is a proportionality constant, T is the absolute temperature, m is the molecular mass and S is the molecular cross-section. It will be recognized that the simple kinetic formula represented by equation Eq. (3) shows no thermal conductivity dependence on the number density of the gas, or pressure. However, it should be appreciated that the driving parameters of the equation are mass and molecular cross-section, and that since hydrogen, $H_2$, is compact and has a low molecular weight it exhibits a high thermal conductivity which is approximately seven times greater than that of methane $CH_4$. The simple kinetic model of Eq. (3) is only capable of representing thermal conductivity for "perfect" gases which exhibit meager molecular force. The limitations of the kinetic model from Eq. (3) were exhibited under varying pressure conditions. It should be appreciated that the behavior of hydrogen gas closely approaches the conductivity for a "perfect gas", while the conductivity of natural gas is highly dependent on pressure. Therefore, it is preferred that gaseous fuel composition based on thermal conductivity be performed by either retaining substantially fixed conditions of pressure and gaseous fuel temperature, or by measuring gaseous temperature and pressure to be accounted for within the calculations for gaseous fuel composition.

Figure 6:
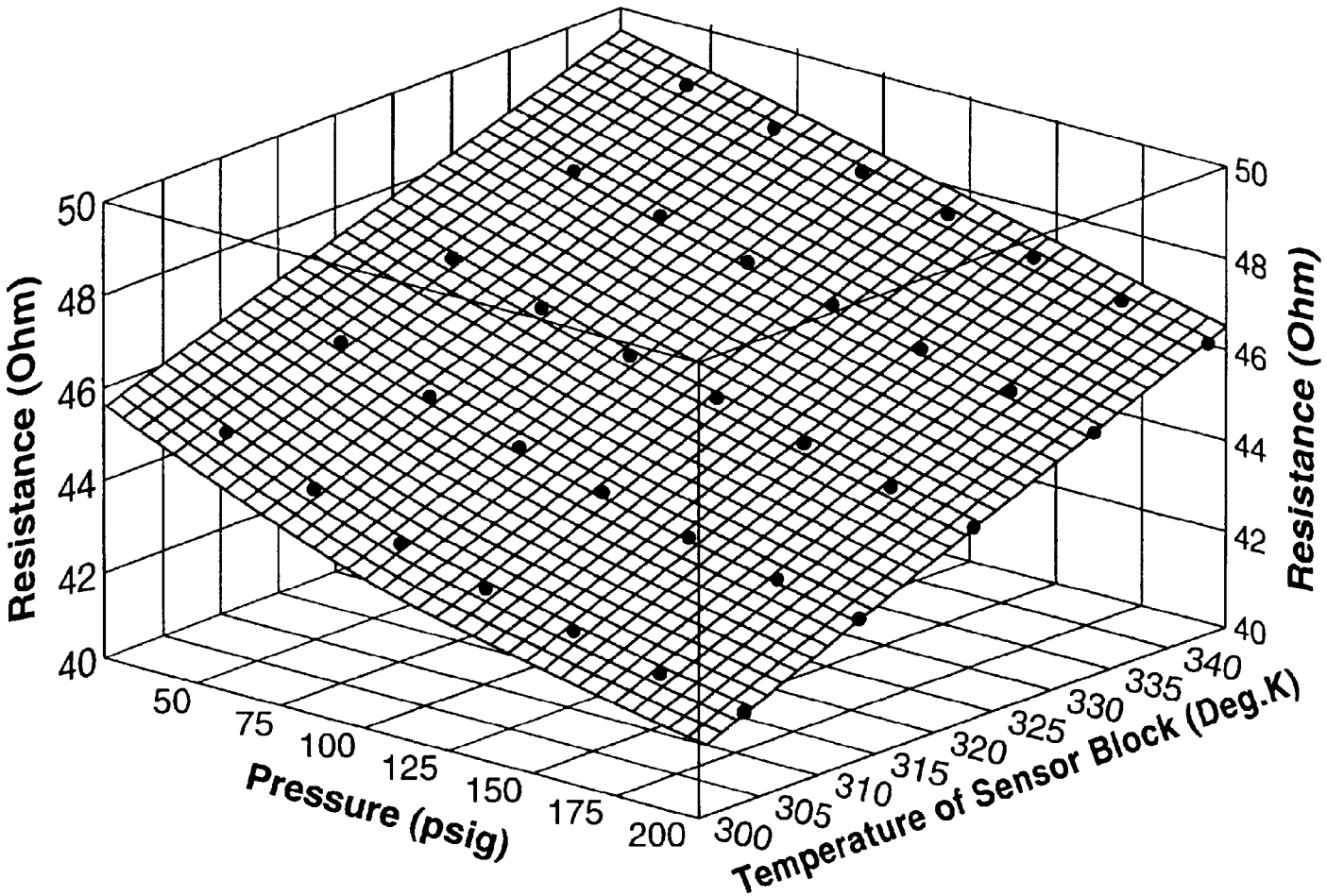
FIG. 6 is a graph showing sensor resistance within a fixed mixture ratio of hydrogen gas and natural gas in response to temperature and pressure changes as determined for an embodiment of the composition sensor within the present invention.

FIG. 6 illustrates a three-dimensional plot of filament resistance as a function of gaseous fuel pressure and sensor block temperature for a gaseous mixture containing 80.03% methane, by mass, with the remaining 19.97% comprising hydrogen.

Figure 7:
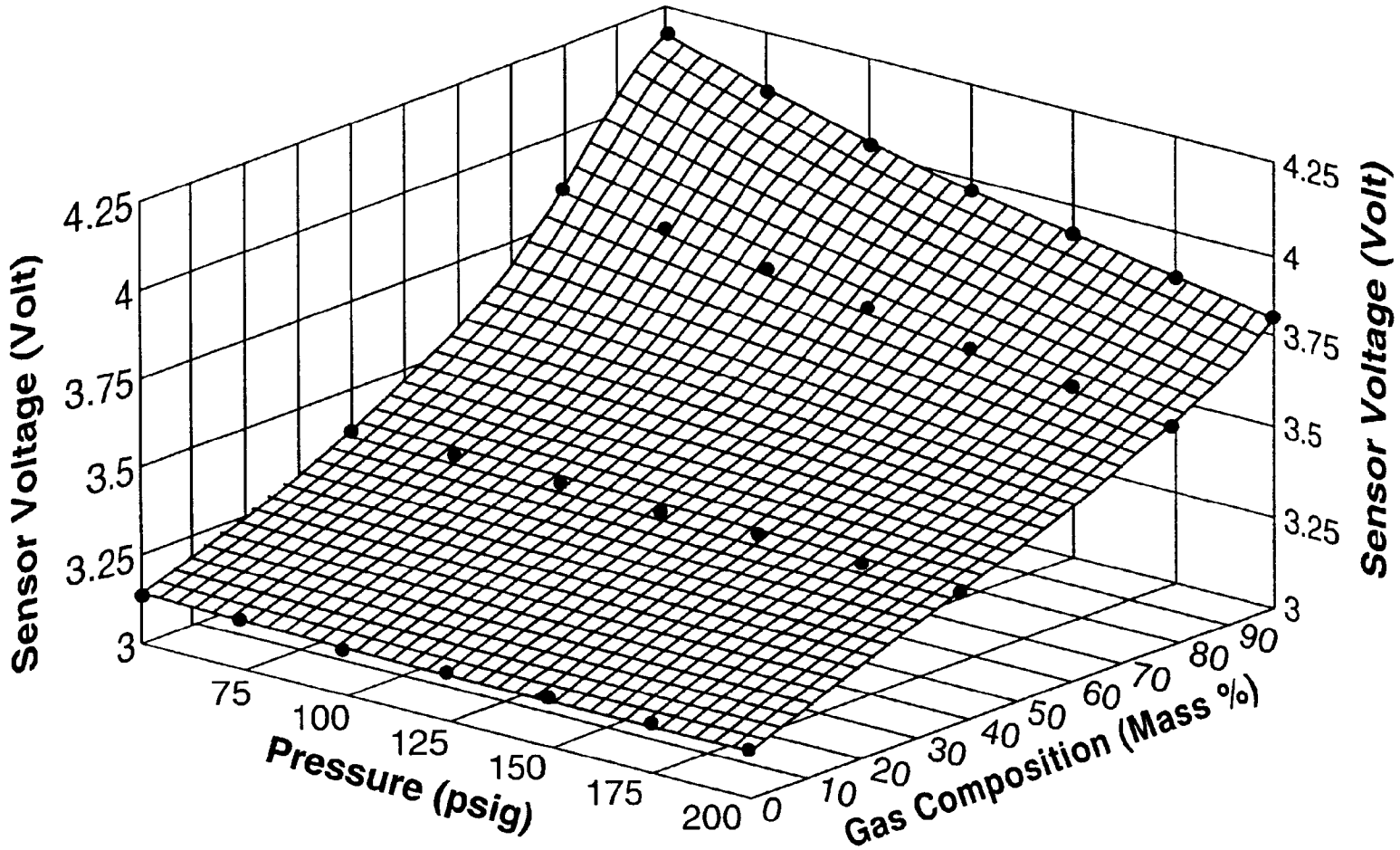
FIG. 7 is a graph showing sensor voltage in response to gas composition and pressure changes as determined for an embodiment of the composition sensor within the present invention.
Figure 8:
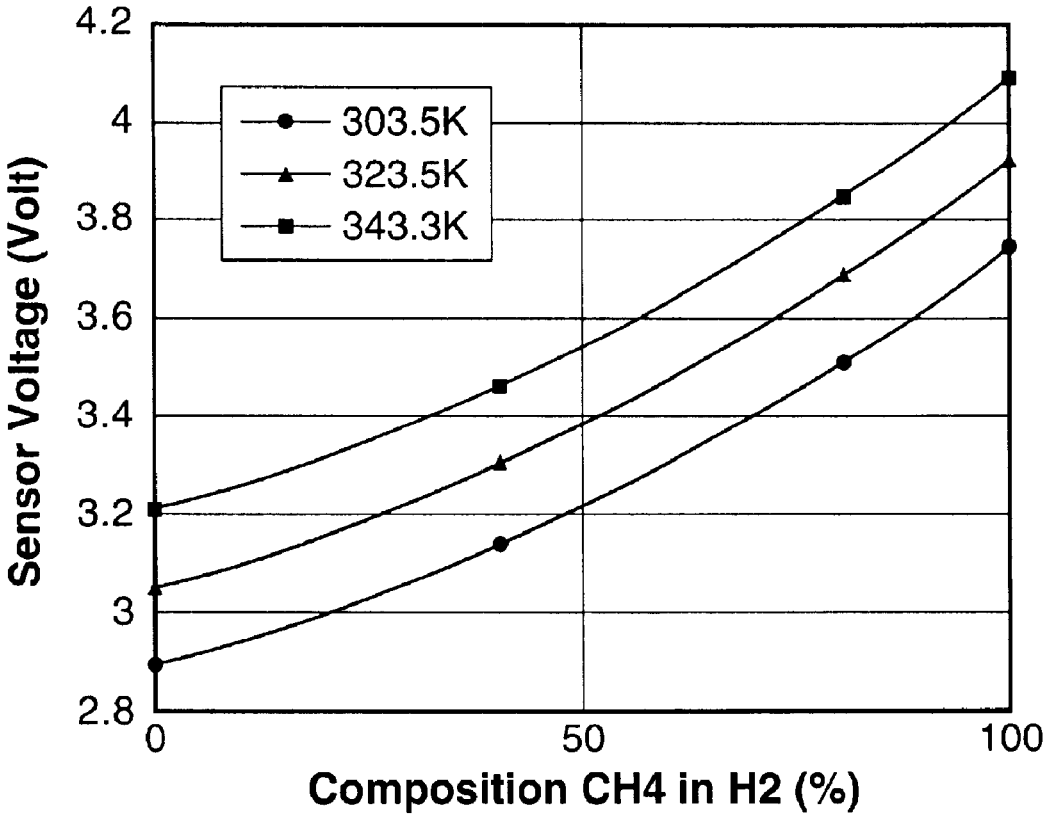
FIG. 8 is a graph showing gas composition as determined from mixture sensor voltage at selected temperatures as determined for an embodiment of the composition sensor within the present invention.

FIG. 7 illustrates gaseous fuel composition, expressed as a methane percentage, as a function of the gaseous pressure and measured sensor voltage. The gaseous fuel composition was determined at a stable sensor body temperature of 60° C. FIG. 8 is a plot of gaseous fuel composition as a function of measured sensor voltage at three absolute temperature values for the sensor body, wherein the pressure is maintained at 100 psig. Gaseous fuel composition, C, may be determined from a three dimensional curve fitting algorithm, which can be developed using multi-variable regression analysis.

$$C=f(P,T,E) \tag{4}$$

The composition C is therefore given by the three dimensional curve fitting equation as a function of Kelvin temperature T, pressure P (psig), and sensor voltage (electromotive force in volts) E.

Utilizing the three-dimensional curve fitting algorithm, the composition of a given fuel mixture may be determined. Fuel composition testing using this approach yielded a worst case error level of approximately 2% (±1%), which should provide a suitable level of accuracy from which to modulate engine combustion parameters. Although the composition of the gaseous fuel may be readily calculated from a curve fitting approach, it should be appreciated that gaseous fuel composition may be determined from any number of alternative measurement calibration techniques, curve mapping techniques, and/or equation-based compensation techniques without departing from the teachings of the present invention.

Figure 9:
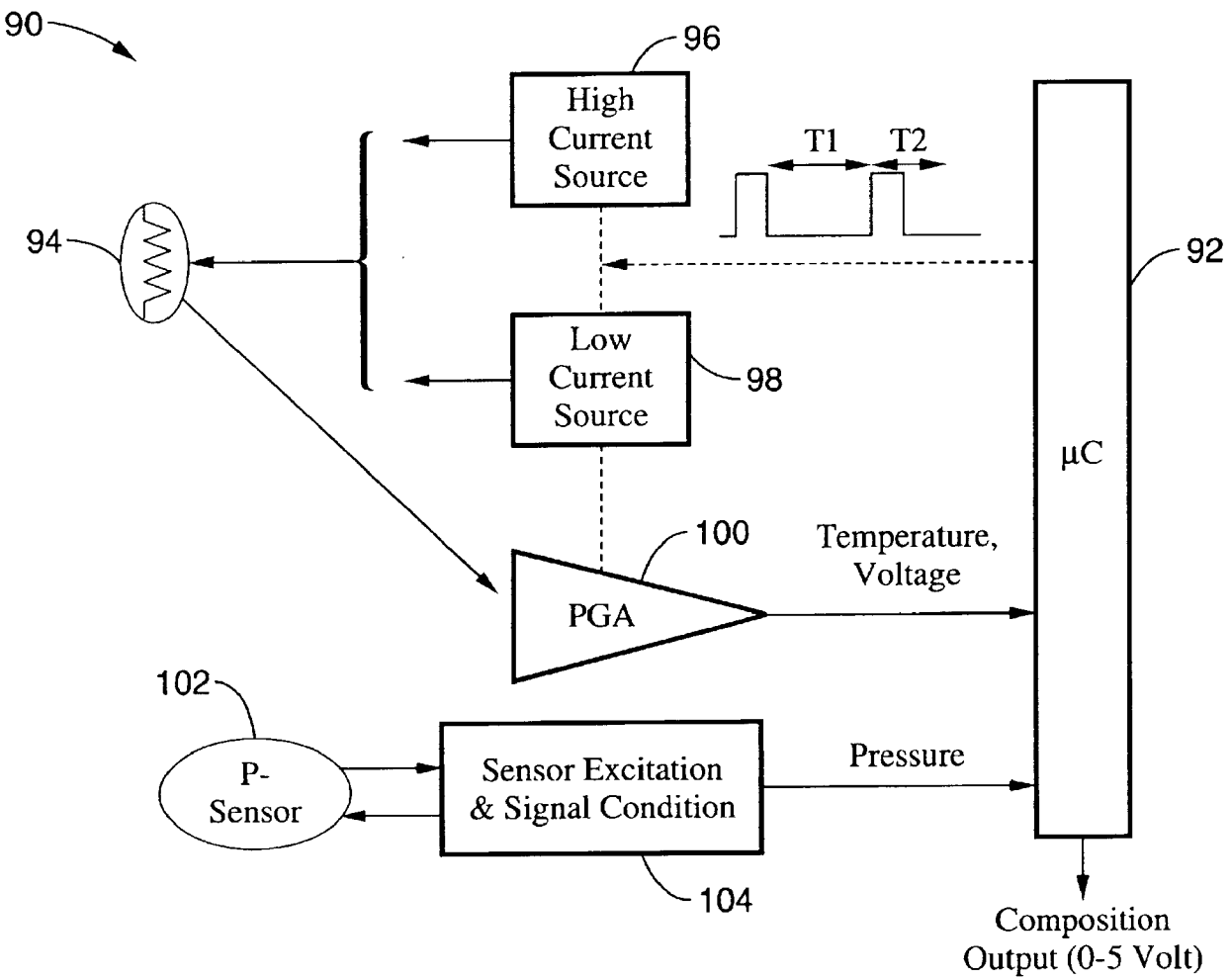
FIG. 9 is a block diagram of a gaseous mixture sensor according to an aspect of the present invention, shown with a microprocessor for calculating a gaseous fuel composition (mixture ratio) value from sensor measurement data.

FIG. 9 exemplifies an embodiment of a gaseous fuel composition sensor system 90 for use within an ICE so that combustion parameters may be adjusted as a function of the mixture ratio of natural gas (methane) to hydrogen. The block diagram contains a digital control circuit 92, shown as a microcontroller, that interfaces to analog current sources and sensor circuits. The sensor circuits 90 are capable of generating multiple current levels through sensor filament 94, which are represented by a high-current source 96 and a low-current source 98 controlled by microcontroller 92. The voltage induced on filament 92 from the application of a predetermined current level is amplified by a programmable gain amplifier 100 whose output is registered by an analog-to-digital converter within microcontroller 92.

The application of low currents to filament 94 allows for the computation of gas temperature which can be used to compensate fuel composition computations. To achieve accurate temperature readings, it will be appreciated that the low current being applied to filament 94 should be insufficient to significantly elevate the filament temperature above the gaseous fuel temperature. The determination of gaseous fuel temperature in this manner should be performed only after the current through filament 94 has been reduced and the temperature of filament 94 has substantially attained thermal equilibrium with the temperature of the surrounding gaseous fuel mixture.

Application of higher current levels to filament 94 can sufficiently heat the filament above the temperature of the gaseous fuel to allow the thermal conductivity of the gaseous fuel composition to be determined under the given set of gas temperature and pressure conditions. Switching between current levels is preferably performed by the microcontroller which toggles between a low current value as set by interval T1 and a high current value subject to interval T2. It will be appreciated that the dual-current sensor mode eliminates the necessity for a separate gas temperature sensor within the circuit, while the decreased average filament provides the additional advantage of prolonging the service life for filament 94. The present embodiment is configured to adapt to a low rate of change for fuel composition, wherein the measurement intervals provide an interval of low current T1 for a period of fifty seconds (50 S), alternating with an interval of high current T2 for a period of ten seconds (10 S). The selected timing of filament drive current and voltage sensing provides for the registration of the available fuel composition when the engine is started, and it updates that reading every minute thereafter. If a particular application warrants more frequent fuel composition updates, faster sampling may be adopted subject to thermal equilibrium limitations. One method of reducing the time to reach thermal equilibrium within each interval is by utilizing a filament which exhibits a lower thermal mass. Another method would be to incorporate a separate temperature sensor, wherein the filament may be continuously utilized for sensing mixture ratio.

Sensor circuit 90 provides a simple and robust method for determining the gaseous fuel composition so that combustion parameters may be modulated accordingly. The dependability of sensor circuit 90 is crucial, and it is preferable that failures and errors within any single component within the system should not prevent VGF engine operation. It should be appreciated that improper sensing of gaseous fuel composition could render the associated engine inoperable, depending on available fuel composition, because of the large disparity between the energy density characteristics of hydrogen and natural gas. For example, attempting to operate the engine from a hydrogen gas source using combustion parameters set for natural gas operation would result in an insufficient power output along with possibly adverse spark timing, due to the more rapid combustion of hydrogen. Therefore, the advantages which accrue from providing circuit redundancy should be appreciated, and may be incorporated herein without departing from the teachings of the present invention. By way of example, redundant sensor filaments may be utilized, such as three filaments, that can allow the VGF engine to continue operating correctly despite failures or errors which occur within any one sensor. For example, a set of three filaments may be driven out of phase with one another and the outputs read by the microcontroller which is capable of executing a voting scheme to eliminate erroneous readings and to preferably generate a trouble indication upon detecting sensor readings that do not agree with one another. Furthermore, other elements, such as the microcontroller and other sensors also may be redundantly configured to enhance dependability.

The digital controller is exemplified as a Z180 32-bit microprocessor, from Zilog Corporation, having a 9 MHz clock, Z84C20 PIO, 128K flash memory and a TLC2543 8 channel 12 bit A/D converter for measuring the sensor signals. An AD7302 2 channel 8 bit D/A converter from Analog Devices Incorporated was utilized for controlling the fuel composition output signal which determines the engine combustion parameters in response to the available mixture ratio. Software routines embedded within the firmware of the microprocessor are preferably utilized for controlling the switching of filament current and for the calculation of the available gaseous fuel composition. The microprocessor preferably solves a three-dimensional equation to determine gaseous fuel composition. A small routine can easily be written in the C language or other programming language for performing the composition analysis described herein. VGF fuel composition may be conveniently measured by the described use of thermal conductivity sensing, or by measuring other differentiable gas characteristics. Upon determining the gaseous fuel composition, a fuel composition signal is communicated to an engine control module (ECM) to control fuel metering, injection, and preferably the ignition timing.

Figure 10:
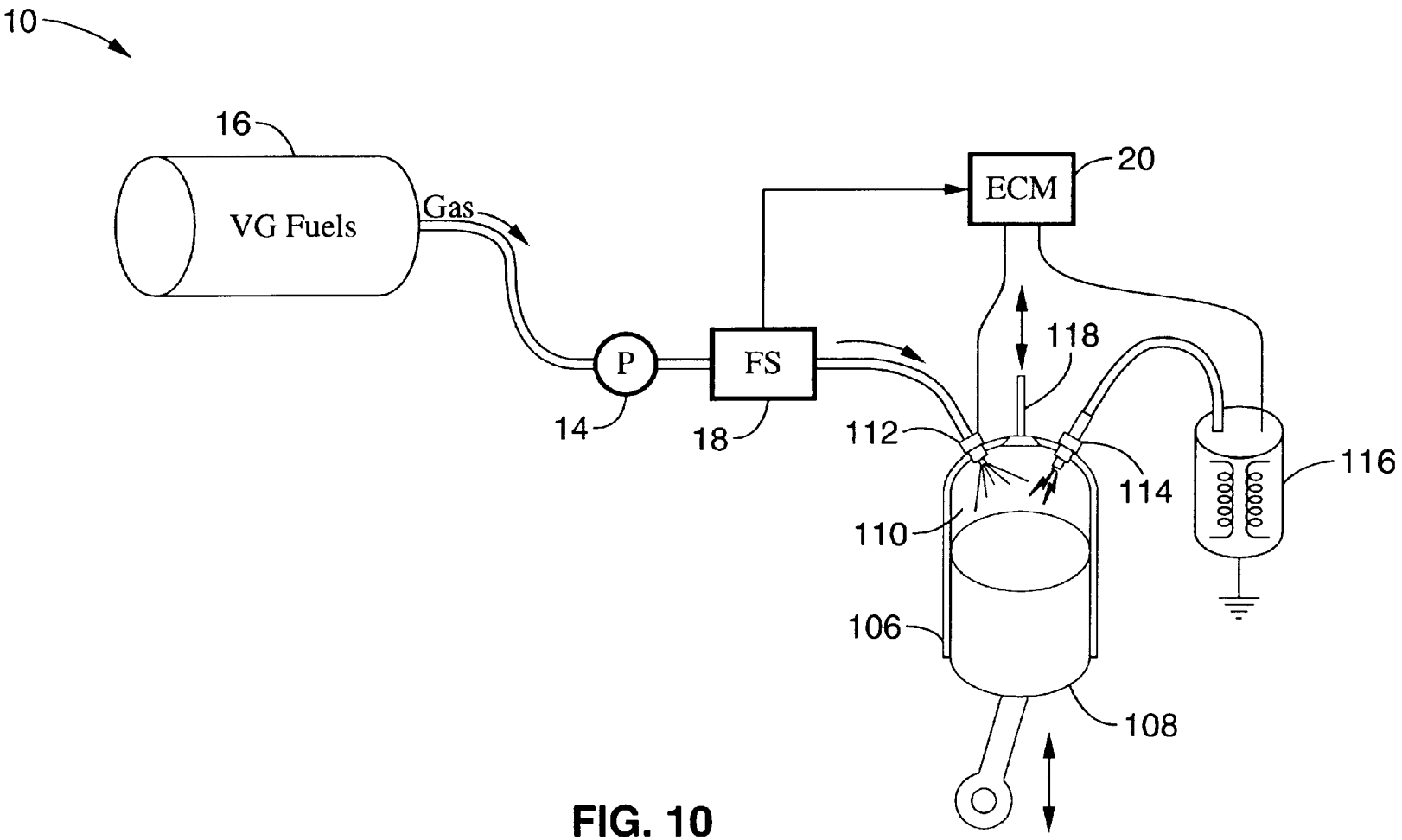
FIG. 10 is a schematic diagram of an variable gaseous fuels engine configured for operation with variable gaseous fuels according to an embodiment of the present invention, showing the modulation of fuel metering and ignition timing in response to the gaseous fuel composition.

FIG. 10 represents a combustion chamber, such as within an internal combustion engine configured for VGF operation according to the present invention. A cylinder 106 is shown with slidably engaged piston 108 above which is a combustion chamber 110 that has a volume responsive to the movement of piston 108 within cylinder 106. Gaseous fuel is metered into combustion chamber 110, filled with oxygen-containing ambient air. The gaseous fuel is introduced into the air of the combustion chamber by a fuel metering device 112, shown as an electronic fuel injector. As the piston reaches the uppermost limit of its travel, generally referred to as "top-dead-center", a spark is introduced by a spark plug 114 within combustion chamber 110 to ignite the combination of gaseous fuel and oxygen which upon expansion drives piston 108 downward thus generating mechanical power. Fuel metering device 112, and optionally the timing of ignition by spark plug 114 through ignition coil 116, are shown controlled by electronic control module (ECM) 20. The control outputs from ECM 20 operate within the present invention in response to the detected composition of the gaseous fuel from fuel source 16 which may contain hydrogen gas, natural gas, or any mixture thereof. Prior to receipt by the fuel metering device, gaseous fuels from fuel source 16 passes through pressure regulator 14 and gaseous fuel composition sensor 18. A combination of valves 118 is represented in the figure and would typically comprise intake valves through which air is received prior to combustion, and exhaust valves through which combustion by-products are later exhausted. It will be appreciated that ECM 20 may be optionally configured to control a number of additional combustion parameters, such as the activation of intake and exhaust valves. In general, the electronics utilized for controlling conventional engine operations are designed to optimize engine efficiency and reduce the level of pollutants emitted. Consistent with these goals the ECM described for use within the present invention incorporates a fuel composition sensor for operation from variable gaseous fuels, while retaining the conventional incorporation of sensors to evaluate other relevant engine state information, such as throttle setting. The ECM utilizes the collected information, such as selecting appropriate "maps", from which it adjusts the operation of all the engine devices under its control. It will be appreciated that controlling a larger number of combustion parameters leads to increased engine efficiency and/or reduced emission levels. It will be further appreciated that the present invention may be implemented on many forms of internal combustion engine, including rotary-engines, Sterling engines, and so forth.

As can be seen, therefore, vehicles manufactured with an engine capable of operating from "variable gaseous fuels" (VGF) according to the present invention may be fueled from facility-based hydrogen generation facilities and existing natural gas distribution facilities. Variable gaseous fuels as described herein comprise either hydrogen gas, natural gas, or any arbitrary mixture of the two gases. VGF operation is particularly attractive for use within hybrid combustion/electric vehicles.

The present invention provides an engine which automatically "self-adapts" to arbitrary percentages of hydrogen in the gas mixture, wherein a single gaseous fuel reservoir can be used to contain this "variable gaseous fuel" which may contain a mixture of whatever natural gas or hydrogen gas fuel was available at refueling. The heat value, flame velocity, and transport properties of the combusted gaseous fuel can vary by nearly an order of magnitude depending on the proportion of hydrogen gas and natural gas being utilized. Thus, substantial changes to the combustion variables are required to achieve efficient operation from a mixed composition fuel.

Operation of an ICE from multiple admixed gases presumes that the combination results in a substantially stable mixture that is not prone to reaction or separation within the gaseous fuel reservoir. Hydrogen gas does not react with components of natural gas and mixtures of the two gases provide a stable composition. To achieve smooth operation from any variable gaseous fuel it is preferred that the fuel be uniformly blended so that the combustion process need not rapidly adapt to the spurious receipt of un-mixed quantities of the fuel gases. It should be appreciated that the typical methods of filling a gaseous fuel tank from a high pressure gaseous source introduces turbulence within the fuel tank due to inrushing gas that should initiate rapid mixing. However, even if the two gaseous components are brought together without initial mixing, it should be appreciated that the diffusion time constant for the gases is short and thereby a uniform mixture is rapidly attained. The time constant for diffusion may be readily determined from a simple dimensional analysis (or by use of the diffusion equation) which suggests a time constant on the order of $L^2/D_{12}$, where L is an appropriate internal dimension of the containing vessel and $D_{12}$ is the binary diffusion coefficient. For hydrogen-methane, $D_{12}$=0.72 $cm^2$/sec at 298° K. Thus the diffusion mixing times are on the order of 1000 seconds for a 30 cm vessel. This suggests that even in the case of very slow non-turbulent filling of the tank, such as slow overnight filling, the gas will tend to rapidly reach uniformity. Furthermore, the gases are not subject to separation except at temperatures substantially below environmental ambient conditions, such as when the methane gas condenses to a liquid and the hydrogen remains in a gaseous form. It should also be readily appreciated that at typical ambient conditions, the gaseous combination would not be subject to separation due to the effects of gravity. At typical ambient temperatures, density changes caused by gravity may be accurately represented by an exponential relationship having a scale height proportional to kT/mg, where k is the Boltzman's constant, m the molecular mass, and g the gravitational constant. For air, the scale height is about 10 km, for methane 14.5 km, and for hydrogen near 100,000 meters. Hence the gravity effect on density is less than one part per thousand at normal temperatures. Finally, it should also be appreciated that the VGF engine is preferably configured for continuous adaptation to the available gaseous fuel composition from the gas fuel source, wherein minor non-uniformities in the gas composition may be compensated for.

Accordingly, it will be seen that this invention provides an apparatus and method for operating internal combustion engines on any arbitrary mixture of hydrogen and natural gas. The present invention includes means for sensing gaseous fuel composition and controlling the parameters of combustion, such as fuel metering and ignition timing, wherein the engine can attain high operating efficiencies from any mixture of gaseous fuel which largely comprises hydrogen gas, natural gas, or any combination thereof, along with any of various additives or impurities. While a thermal conductivity sensor is preferably used as a means for determining the available gaseous fuel composition so that the combustion parameters of the engine may be properly modulated, the invention contemplates other means of characterizing the fuel mixture using one or more alternative measurements that register a differentiable characteristic of the subject gases. Furthermore, while modulation of combustion parameters preferably comprises changing the amount of fuel being metered to the engine and optionally the ignition timing, and/or valve timing, to optimize engine operating efficiency, it will be appreciated that a number of additional engine operating parameters may be adjusted in response to changes in the composition of the gaseous fuels without departing from the present invention.

It will be readily appreciated that the availability of vehicles whose fuel storage tanks may be filled with quantities of either natural gas or hydrogen would greatly simplify the infrastructure problems associated with adopting renewable hydrogen as a new fuel source. Vehicles which incorporate VGF engines can utilize either form of gas, wherein the driver may select a type of gaseous fuel to be used in response to factors such as availability and/or cost. In general, the use of natural gas by itself provides maximum range and power due to its inherently higher energy density, while the use of hydrogen gas by itself provides substantially lowered emissions and eventually a lowered cost factor. The range, power, cost, and emissions available from blending the two gaseous fuels being dependent on the specific mixture ratio being combusted. It will be further appreciated that upon equipping vehicles with VGF engines, fuel distributors may elect to sell either, or both, forms of gaseous fuel. These fuels could be distributed separately or in any desired mixture ratio. Furthermore, gas refueling equipment at fuel distribution facilities could be configured with gas composition sensors, such as a thermal conductivity sensor according to described aspects of the present invention, whereby hydrogen gas and natural gas may be dispensed in combination to achieve a user specified mixture ratio within their fuel tank according to desired performance and cost factors.

Utilizing a vehicle equipped for operation from variable gaseous fuels thereby provides the flexibility to operate from home-generated hydrogen gas supplies or any available mixture of hydrogen gas and natural gas that is available from a fueling station. Utilizing the teachings of the present invention, therefore, can provide for creating VGF engines that provide a smooth fuel migration path for both vehicle manufacturers and fuel distributors from a high-emission non-renewable fossil fuel source to a clean renewable fuel source.

A number of advantages also accrue from manufacturing vehicles capable of VGF operation. A migration path is provided with VGF technology from the current use of less costly hydrocarbon fuels, to a renewable source of energy that can be generated domestically. Any ICE having at least one combustion chamber that is capable of burning gaseous fuels may be configured to operate on a variable gaseous range of fuels according to the present invention, and can he produced at a modest cost premium over present day non-VGF operable engines. A VGF engine operating on pure hydrogen, and configured with exhaust gas recirculation and catalytic scrubbing to remove the remaining $NO_x$, should be capable of meeting the criterion imposed by zero emission standards.

Note also that the ability to perform home refueling, such as by using a "personal fueling appliance" (PFA), can provide a low-cost home refueling capability similar to the charging of an electric car. In contrast to an electric vehicle, however, the range of a VGF equipped vehicle can be extended indefinitely with natural gas that is currently available at many vehicle refueling stations. One proposed PFA is designed in a form factor that approximates the size of a clothes-washer and requires only a supply of water and electricity to generate a 300 bar (over 4000 psig) source of hydrogen. Natural gas refueling is available internationally and provides a base level of infrastructure for the distribution of gaseous fuels upon which hydrogen distribution may be built. VGF engines being capable of operating from any mixture of available hydrogen and natural gas are ideally suited for utilizing gases generated from land-fill or digesters due to an inherent insensitivity to impurities. It should be appreciated that generated gas fuel sources typically contain levels of impurities which may damage or otherwise hinder proper fuel cell operation. Internal combustion engines adapted with sensors and combustion controls to achieve VGF operation provide a bridge between current non-renewable energy sources and environmentally friendly renewable energy sources. Sales of VGF equipped vehicles would stimulate the further development of a renewable hydrogen energy refueling infrastructure that could eventually support additional technologies, such as vehicles powered from hydrogen fuel cells when that technology matures. The early introduction of hydrogen for fueling VGF vehicles would provide an impetus for establishing a hydrogen infrastructure that includes both physical facilities and the adoption of new fueling codes and regulations.

Although the description above contains many specificities, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A variable gaseous fuels engine, comprising:

an internal combustion engine having a combustion chamber;

said combustion chamber adapted to receive a mixture of a first gaseous fuel and a second gaseous fuel for combustion therein;

means for detecting the ratio of said first and second gaseous fuels in said mixture and generating a fuel composition signal in response to said detected ratio; and an engine control module;

said engine control module adapted to modulate the quantity of said gaseous fuel mixture received within said combustion chamber in response to said fuel composition signal;

wherein said engine is thereby capable of operating from any arbitrary mixture of said first and second gaseous fuels.

2. A variable gaseous fuels engine as recited in claim 1, wherein said gaseous fuel composition detecting means comprises:

an electronic sensor;

said electronic sensor adapted to differentiate one or more characteristics of hydrogen from one or more characteristics of natural gas.

3. A variable gaseous fuels engine as recited in claim 2, wherein said electronic sensor comprises a thermal conductivity sensor.

4. A variable gaseous fuels engine as recited in claim 3, wherein said thermal conductivity sensor comprises:

a housing having a passageway through which said gaseous fuel can flow; and a thermal conductivity sensor element positioned within said passageway;

said thermal conductivity sensor clement adapted to make fluidic contact with said gaseous fuel.

5. A variable gaseous fuels engine as recited in claim 4, wherein said housing is maintained at a substantially constant temperature.

6. A variable gaseous fuels engine as recited in claim 4, wherein said thermal conductivity sensor element comprises a filament through which a first electrical current is passed for the registration of thermal conductivity for said gaseous fuel with which it is in contact.

7. A variable gaseous fuels engine as recited in claim 5:

wherein said first electrical current is of sufficient amperage to heat said filament to a temperature exceeding the temperature of said gaseous fuel; and wherein the thermal conductivity of said gaseous fuel is determined from analyzing the conductive heat dissipation which occurs to moderate the elevation of filament temperature.

8. A variable gaseous fuels engine as recited in claim 7, wherein said first electrical current is in excess of one milliampere.

9. A variable gaseous fuels engine as recited in claim 7, wherein said first electrical current is less than approximately two hundred milliamperes.

10. A variable gaseous fuels engine as recited in claim 7:

wherein the amount of said filament heating is detected by registering electrical resistance of said filament;

said resistance comprising the quotient of filament voltage divided by said first current induced in said filament.

11. A variable gaseous fuels engine as recited in claim 10, wherein conductivity of the gaseous mixture is determined from the amount of filament temperature moderation which occurs in response to conductive energy losses.

12. A variable gaseous fuels engine as recited in claim 6, wherein said filament comprises a metallic material.

13. A variable gaseous fuels engine as recited in claim 12, wherein said metallic material substantially comprises tungsten.

14. A variable gaseous fuels engine as recited in claim 13, wherein said filament contains an operable quantity of Rhenium.

15. A variable gaseous fuels engine as recited in claim 14, wherein said quantity of said Rhenium is up to approximately ten percent.

16. A variable gaseous fuels engine as recited in claim 14, wherein said quantity of Rhenium is greater than approximately two percent.

17. A variable gaseous fuels engine as recited in claim 4, wherein said filament is positioned in a chamber that is in fluid communication with said passageway.

18. A variable gaseous fuels engine as recited in claim 17, wherein said filament is positioned within said chamber a predetermined offset distance from the center of said passageway.

19. A variable gaseous fuels engine as recited in claim 18, wherein said predetermined offset distance is in relation to the diameter of said chamber.

20. A variable gaseous fuels engine as recited in claim 19, wherein said offset distance is given by a distance approximately equivalent to four times the diameter of said chamber.

21. A variable gaseous fuels engine as recited in claim 18:

wherein the diameter of said chamber is approximately one-half centimeter; and wherein the distance from the center of said passageway to said filament is approximately 2.3 centimeters.

22. A variable gaseous fuels engine as recited in claim 1, further comprising:

a pressure regulator;

said pressure regulator adapted to regulate pressure of said gaseous fuel flowing to said combustion chamber.

23. A variable gaseous fuels engine as recited in claim 22:

wherein said pressure regulator is adapted to reduce the gaseous fuel pressure to a predetermined value; and wherein the predetermined value of fuel pressure is consistent with proper modulation of gaseous fuel quantity by said engine control module.

24. A variable gaseous fuels engine as recited in claim 23, wherein said predetermined value is approximately one hundred forty-five pounds per square inch.

25. A variable gaseous fuels engine as recited in claim 4, further comprising means for registering the temperature of said gaseous fuel whose conductivity is being registered by said thermal conductivity sensor.

26. A variable gaseous fuels engine as recited in claim 25:

wherein the temperature of said gaseous fuel is measured by passing a second current through said filament;

wherein said second current is substantially less than said first current; and wherein the voltage expressed across said filament by said second current is substantially indicative of the temperature of said filament in substantial thermal equilibrium with said surrounding gaseous fuel.

27. A variable gaseous fuels engine as recited in claim 26, wherein said second current is less than approximately ten milliamperes.

28. A variable gaseous fuels engine as recited in claim 27, wherein said second current is approximately one milliampere.

29. A variable gaseous fuels engine as recited in claim 1, wherein said engine control module is adapted to control ignition timing within said combustion chamber in response to said fuel composition signal.

30. A variable gaseous fuels engine as recited in claim 1:

wherein said engine control module is adapted for scaling the amount of fuel being metered to said combustion chamber under current operating conditions;

wherein the scaling of the fuel amount to said combustion chamber is based on an estimation of the energy density contained in said gaseous fuel mixture; and wherein the composition of said gaseous fuel mixture has been communicated by the receipt of said fuel composition signal.

31. A variable gaseous fuels engine capable of operating from a variable mixture of hydrogen gas and natural gas, comprising:

an internal combustion engine having a combustion chamber;

said combustion chamber adapted to receive a mixture of a first gaseous fuel and a second gaseous fuel for combustion therein;

a thermal conductivity sensor;

said thermal conductivity sensor adapted to generate a fuel composition signal indicative of the ratio of said first and second gaseous fuels in said mixture; and an engine control module;

said engine control module adapted to modulate said quantity of said gaseous fuel mixture received within said combustion chamber in response to said fuel composition signal;

wherein said engine is thereby capable of operating from any arbitrary mixture of said first and second gaseous fuels.

32. A variable gaseous fuels engine as recited in claim 31, wherein said engine control module is adapted to modulate ignition timing in response to changes in gaseous fuel composition as indicated by said fuel composition signal.

33. A variable gaseous fuels engine as recited in claim 31, wherein said thermal conductivity sensor comprises:

a housing having a passageway through which gaseous fuel can flow; and a thermal conductivity sensor element positioned within said passageway.

34. A variable gaseous fuels engine as recited in claim 33, wherein said housing is maintained at a controlled temperature.

35. A variable gaseous fuels engine as recited in claim 33:

wherein said thermal conductivity sensor element comprises an electrical filament; and wherein a first electrical current is passed through the filament for sensing the thermal conductivity of said gaseous fuels in contact therewith.

36. A variable gaseous fuels engine as recited in claim 35:

wherein said first electrical current is of sufficient amperage to heat said filament to a temperature which is elevated above that of said gaseous fuel mixture;

whereby the thermal conductivity of said gaseous fuel mixture is determined.

37. A variable gaseous fuels engine as recited in claim 36, wherein said first electrical current exceeds approximately one milliampere.

38. A variable gaseous fuels engine as recited in claim 36, wherein said first electrical current is under approximately two hundred milliamperes.

39. A variable gaseous fuels engine as recited in claim 36:

wherein conductivity of said gaseous mixture is determined from the amount of filament temperature elevation which occurs;

wherein said filament temperature elevation is determined from the resistance of said filament as given by quotient which results from dividing filament voltage by said first filament current.

40. A variable gaseous fuels engine as recited in claim 35, wherein said filament comprises a metallic material.

41. A variable gaseous fuels engine as recited in claim 40, wherein said metallic material substantially comprises Tungsten.

42. A variable gaseous fuels engine as recited in claim 40, wherein said filament comprises less than approximately ten percent Rhenium.

43. A variable gaseous fuels engine as recited in claim 40, wherein said filament comprises greater than approximately two percent Rhenium.

44. A variable gaseous fuels engine as recited in claim 35:

wherein said filament is positioned within a chamber fluidly connected to said passageway; and wherein said chamber is adapted to partially isolate said filament from changes in convective cooling that may occur in response to variations in the gaseous fuel flow rate.

45. A variable gaseous fuels engine as recited in claim 31, further comprising:

a pressure regulator;

said pressure regulator adapted to regulate pressure of said gaseous fuel flowing to said combustion chamber.

46. A variable gaseous fuels engine as recited in claim 45, wherein said pressure regulator is adapted to limits the pressure enroute to said combustion chamber to a predetermined maximum value.

47. A variable gaseous fuels engine as recited in claim 46, wherein said maximum value of pressure is approximately one hundred forty five pounds per square inch.

48. A variable gaseous fuels engine as recited in claim 31, further comprising means for detecting the temperature of the gaseous fuel whose thermal conductivity is to be registered by said thermal conductivity sensor.

49. A variable gaseous fuels engine as recited in claim 48:

wherein the temperature of said gaseous fuel is measured by passing a second current through said filament within said thermal conductivity sensor;

wherein said second current is substantially less than said first current; and wherein the voltage induced in the filament by said second current is substantially indicative of the temperature of the filament in substantial thermal equilibrium with the surrounding gaseous fuel.

50. A variable gaseous fuels engine as recited in claim 49, wherein said second current is less than approximately ten milliamperes.

51. A variable gaseous fuels engine as recited in claim 50, wherein said second current is approximately one milliampere.

52. A variable gaseous fuels engine as recited in claim 31, wherein said engine control module is adapted to vary ignition timing of said internal combustion engine in response to the determined fuel composition.

53. A variable gaseous fuels engine as recited in claim 31:

wherein said engine control module is adapted to modulate the amount of fuel being metered to said combustion chamber; and wherein fuel metering is based on an estimation of the energy density contained in said gaseous fuel mixture whose composition has been determined.

54. In an internal combustion engine configured for generating mechanical energy by the combustion of a gaseous fuel mixture of first and second gaseous fuels, the improvement comprising:

a fuel composition sensor positioned for contacting said gaseous fuel mixture;

said fuel composition sensor adapted to generate a gaseous fuel composition signal indicative of the ratio of said first and second gaseous fuels in said gaseous fuel mixture; and an engine control module;

said engine control module adapted to modulate said quantity of said gaseous fuel received within said combustion chamber in response to said fuel composition signal;

wherein said engine is thereby capable of operating from any arbitrary mixture of said first and second gaseous fuels.

55. An improved internal combustion engine as recited in claim 54, wherein the gaseous fuel composition substantially comprises hydrogen gas, or natural gas, or any combined mixture of hydrogen and natural gas.

56. An improved internal combustion engine as recited in claim 54:

wherein said fuel composition sensor comprises a sensor capable of registering a differentiable characteristic of the admixed constituents of said gaseous fuel; and wherein said differentiable characteristic is substantially indicative of fuel composition.

57. An improved internal combustion engine as recited in claim 56, wherein said differentiable characteristic is registered by a thermal conductivity sensor positioned for contact with said gaseous fuel.

58. An improved internal combustion engine as recited in claim 57:

wherein said thermal conductivity sensor comprises a heated filament retained in contact with said gaseous fuel; and wherein the temperature of said heated filament in relation to the temperature of said gaseous fuel is utilized as an indicator of the thermal conductivity of said gaseous fuel which is in contact with said heated filament.

59. A fuel composition sensor capable of communicating a differentiable characteristic between at least two gaseous fuels within a gaseous fuel mixture, said characteristic being communicated for receipt by an electronic engine control module within an internal combustion engine that operates subject to the receipt of variable mixtures of gaseous fuel, comprising:

a housing having a passageway through which a gaseous fuel mixture passes prior to receipt by the internal combustion engine;

a filament positioned within said passageway and positioned to establish fluidic contact with said gaseous fuel mixture;

a first electrical current source capable of being connected to said filament;

said first electrical current source capable of inducing sufficient current flow within said filament to increase the temperature of said filament above the temperature of the surrounding gaseous fuel composition; and voltage measurement means configured to register filament voltage and to communicate said filament voltage to an electronic engine control module;

whereby the ratio of a first gaseous fuel and a second gaseous fuel in said gaseous fuel mixture is determined by evaluating the thermal conductivity of said gaseous fuel mixture as a function of filament voltage;

wherein said fuel composition sensor renders said engine capable of operating from any arbitrary mixture of said first and second gaseous fuels.

60. A fuel composition sensor as recited in claim 59, wherein the gaseous fuel comprises a variable gaseous mixture of fuels comprising a first gaseous fuel, or a second gaseous fuel, or an admixed combination of said first gaseous fuel and said second gaseous fuel.

61. A fuel composition sensor as recited in claim 60, wherein said first gaseous fuel comprises hydrogen gas.

62. A fuel composition sensor as recited in claim 60, wherein said second gaseous fuel comprises natural gas.

63. A fuel composition sensor as recited in claim 59, wherein said housing is maintained at a substantially fixed temperature.

64. A fuel composition sensor as recited in claim 59, wherein said first electrical current source is capable of inducing a current in excess of approximately one milliampere within said filament.

65. A fuel composition sensor as recited in claim 59, wherein said first electrical current source is capable of inducing a current less than or equal to approximately two hundred milliamperes within said filament.

66. A fuel composition sensor as recited in claim 59, wherein said filament comprises a metallic material.

67. A fuel composition sensor as recited in claim 66, wherein said metallic material substantially comprises Tungsten.

68. A fuel composition sensor as recited in claim 67, wherein said Tungsten comprises less than approximately ten percent by weight of Rhenium.

69. A fuel composition sensor as recited in claim 67, wherein said Tungsten comprises at least approximately two percent by weight of Rhenium.

70. A fuel composition sensor as recited in claim 59, wherein said filament is positioned within a chamber of said passageway to isolate said filament from the convective influence of said gaseous fuel flow through said passageway.

71. A fuel composition sensor as recited in claim 70, wherein said filament is offset from the center of said passageway by a distance approximately equivalent to four times the diameter of said chamber.

72. A fuel composition sensor as recited in claim 71, wherein the diameter of said chamber is approximately one half centimeter and the distance from the center of the passageway to said filament is approximately two centimeters.

73. A fuel composition sensor as recited in claim 59, further comprising means for registering the temperature of the gaseous fuel surrounding said filament and communicating a signal in response to said temperature for receipt by an electronic engine control module.

74. A fuel composition sensor as recited in claim 73:

wherein said temperature registration means comprises a second electrical current source which is incapable of generating sufficient current to cause substantial filament heating; and wherein gaseous fuel temperature can be determined from the registered filament voltage.

75. A fuel composition sensor as recited in claim 74, wherein said second current is less than approximately ten milliamperes.

76. A fuel composition sensor as recited in claim 75, wherein said second current is approximately one milliampere.

77. A method of operating an internal combustion engine from a variable mixture of gaseous fuels, comprising:

determining the ratio of a first gaseous fuel and a second gaseous fuel in said mixture;

determining an amount of said gaseous fuel mixture to be metered into said internal combustion engine based on said ratio; and adjusting fuel metering of said gaseous fuel mixture into said internal combustion engine based on said ratio;

wherein said engine is thereby capable of operating from any arbitrary mixture of first and second gaseous fuels.

78. A method as recited in claim 77, wherein said gaseous fuel comprises a first gaseous fuel, or a second gaseous fuel, or any admixed combination of said first and said second gaseous fuels.

79. A method as recited in claim 78, wherein said first gaseous fuel comprises hydrogen gas.

80. A method as recited in claim 78, wherein said second gaseous fuel comprises natural gas.

81. A method as recited in claim 78, wherein detecting the composition of the gaseous fuel mixture containing said first and said second gaseous fuel comprises finding the mixture ratio of said first gaseous fuel within said second gaseous fuel.

82. A method as recited in claim 78, wherein the detection of the gaseous fuel composition comprises:

detecting the thermal conductivity of said gaseous fuel being received by said internal combustion engine; and evaluating the relative thermal conductivity contributions of each primary constituent of said gaseous fuel mixture to arrive at a gaseous fuel composition value expressed as a percentage of said first gaseous fuel within said second gaseous fuel.

83. A method as recited in claim 82, wherein detecting thermal conductivity is comprising:

supplying an amount of energy to heat a filament that is retained in contact with said gaseous fuel to a temperature which exceeds the gaseous fuel;

determining the temperature of the heated filament; and determining thermal conductivity from evaluating filament temperature in relation to the supplied energy.

84. A method as recited in claim 83, wherein supplying the energy to heat the filament comprises inducing a predetermined current to flow through the filament.

85. A method as recited in claim 84, wherein determining the temperature of the filament comprises:

detecting the voltage which exists across said filament;

computing filament resistance from ohm's law, R=V/I; and finding the characteristic filament temperature from the computed filament Lance, wherein empirical filament data is used for correlating filament resistance to filament temperature.

86. A method as recited in claim 77, further comprising maintaining gaseous fuel pressure at a substantially constant pressure, whereby the conditions are simplified under which fuel composition is detected.

87. A method as recited in claim 77, further comprising maintaining gaseous fuel temperature at a substantially constant temperature, whereby the conditions are simplified under which the fuel composition is detected.

88. A method as recited in claim 77, further comprising measuring said gaseous fuel temperature to increase the accuracy of detecting the composition of said gaseous fuel.

* * * * *